United States Patent [19]
DeLuccia

[11] Patent Number: 4,675,005
[45] Date of Patent: Jun. 23, 1987

[54] RETRACTABLE DISPOSABLE SYRINGE

[76] Inventor: James DeLuccia, 830 Belmont Ave., North Haledon, N.J. 07508

[21] Appl. No.: 860,844

[22] Filed: May 8, 1986

[51] Int. Cl.⁴ .............................................. A61M 5/32
[52] U.S. Cl. .................................... 604/110; 604/198
[58] Field of Search ............... 128/764, 765; 604/110, 604/196–198, 263, 220, 228

[56] References Cited
U.S. PATENT DOCUMENTS

| | | | |
|---|---|---|---|
| 3,937,211 | 2/1976 | Merten | 604/220 X |
| 4,026,287 | 5/1977 | Haller | 604/110 X |
| 4,425,120 | 1/1984 | Sampson et al. | 604/198 |
| 4,507,117 | 3/1985 | Vining et al. | 604/196 |

Primary Examiner—Dalton L. Truluck
Attorney, Agent, or Firm—Siegmar Silber

[57] ABSTRACT

A disposable syringe for delivery of an injectable fluid having a locking device, so that after use, a hub and cannula of the syringe can be detached from the cylindrical body, withdrawn thereinto, and locked thereto. A plunger of the syringe also functions as a withdrawal mechanism, and in turn, has a tool for this purpose which functions in a cooperative manner with a fitting on the back of the hub. Several embodiments of the withdrawal tool, hub fitting and locking mechanism are described.

22 Claims, 8 Drawing Figures

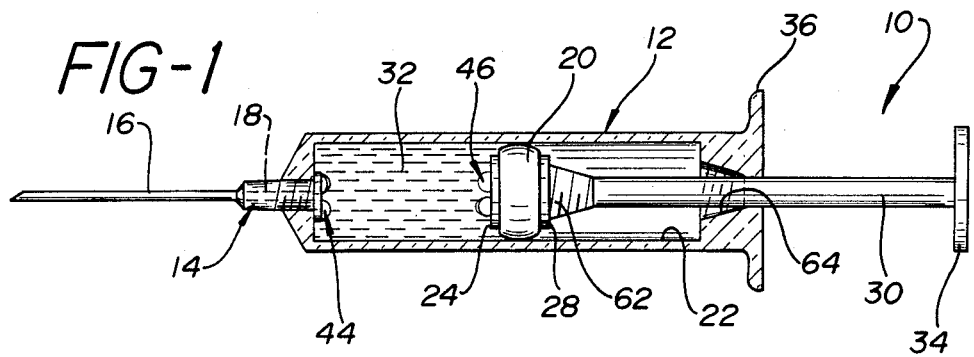
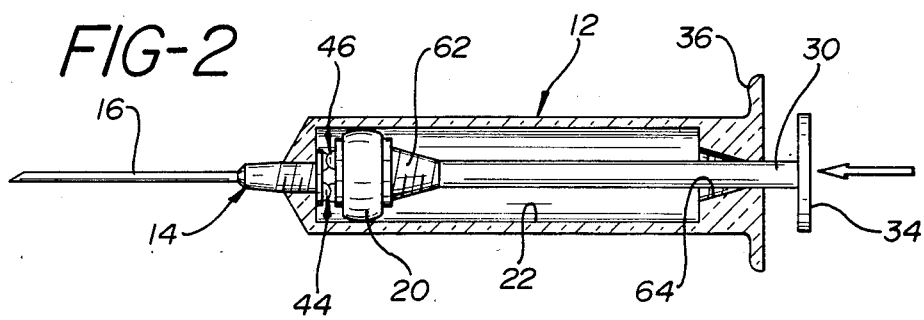
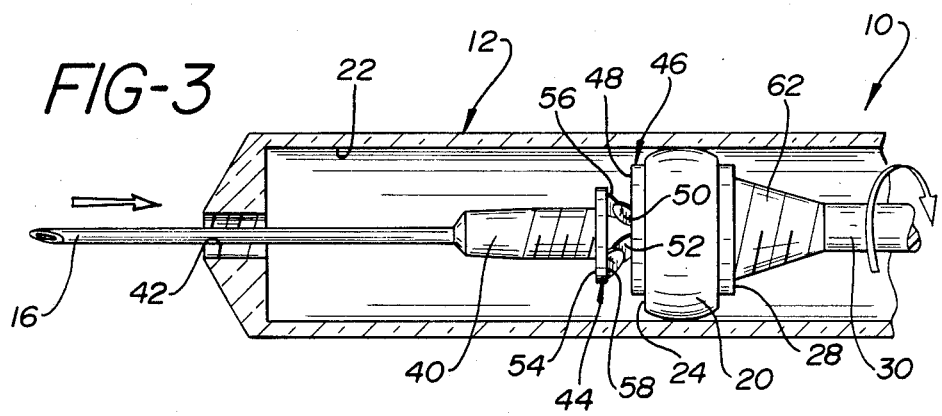
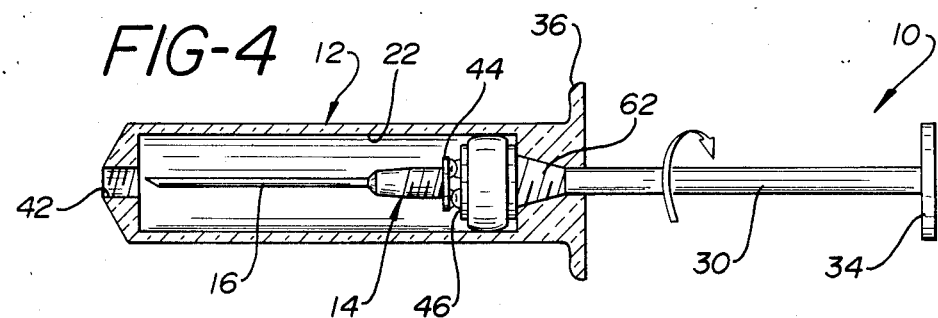

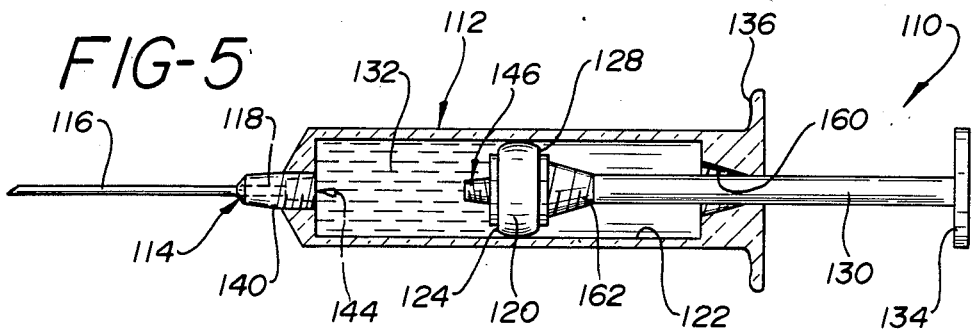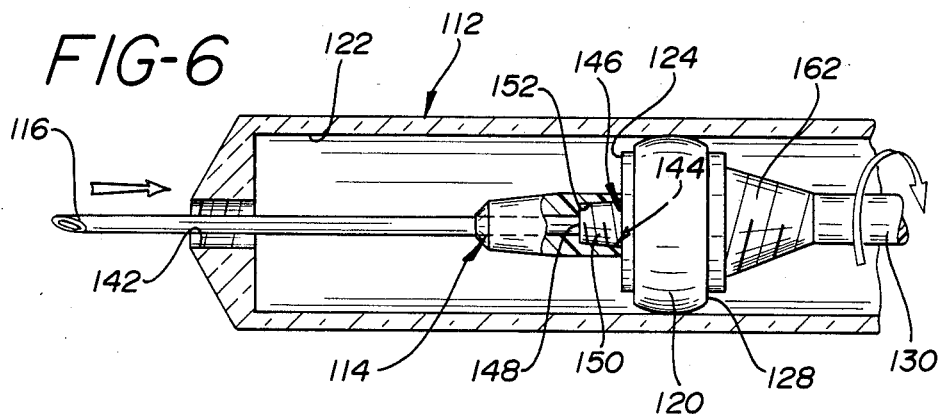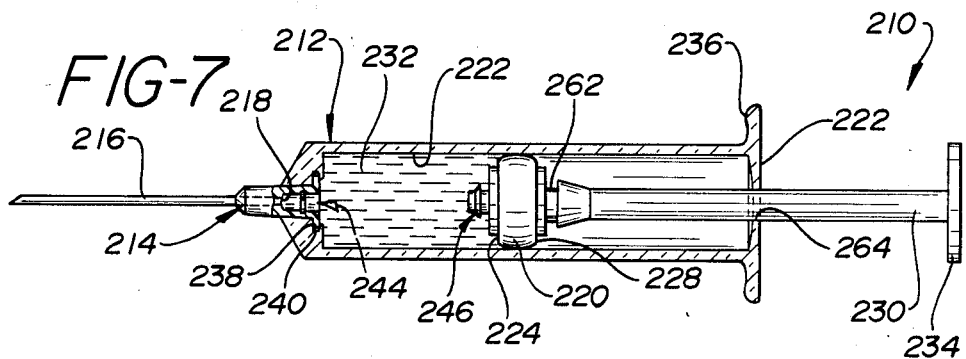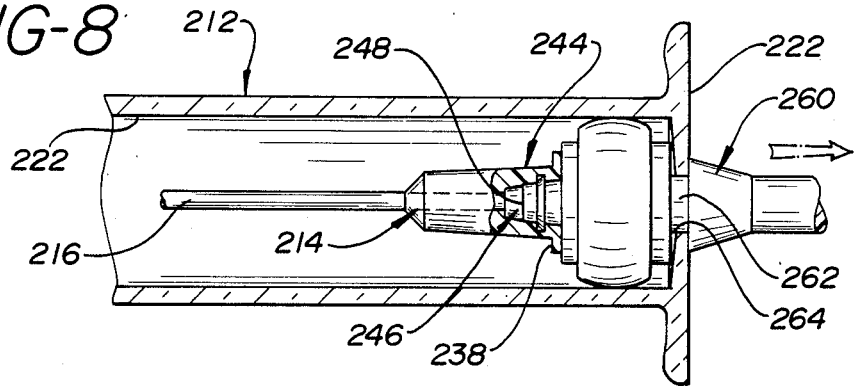

RETRACTABLE DISPOSABLE SYRINGE

BACKGROUND OF THE INVENTION

1. Field of the Invention

This invention relates to an improved retractable syringe having a cannula which after use may be drawn into the barrel portion of the syringe, and, more particularly, a syringe for the hypodermic administration of drugs and other medicinal preparations which, after use, may be discarded. The problem of contact by personnel with contaminated implements is thereby avoided.

2. Information Disclosure Statement

With the advent of the acquired immune deficiency syndrome (AIDS) and the prior problems in health service organizations controlling hepatitis, an improvement in syringe technology is indicated. While prior art has shown a retractable cannula structure several technical problems still remain. Becuase of the medical personnel using syringes, the retractability feature must of necessity be simple, easy to operate, and highly reliable. Furthermore, the present technology has not disclosed a cannula and hub assembly which is mounted retractably within the cylindrical body of the syringe.

In preparation for this application, a pre-examination patentability search was performed in Class 604, subclasses 110 and 195. The search uncovered U.S. Pat. No. 4,026,287 of Irene Haller (originally classified in Class 128/215 and cross-referenced into Class 128/218P). In contradistinction to the application at hand, Haller '287 teaches a frangible structure which structure approaches disposal in a manner readily distinguishable from that which follows.

SUMMARY AND OBJECTS OF THE INVENTION

It is an object of the present invention to provide an improved disposable syringe, which, after the injectible has been expelled, is equipped to store securely the parts thereof that may be contaminated.

It is a further object of the invention to provide such a syringe with an internal hub and cannula and to provide built-in tool for withdrawing these parts into the barrel of the syringe.

It is a yet further object of the invention to provide a locking mechanism to secure the withdrawn parts in a position for disposal.

It is a feature of the present invention to reduce contact of health service workers with, injected contraminated syringes.

It is another feature of the invention to facilitate disposal of used syringes in a simple and economic manner.

SUMMARY

The invention describes a disposable syringe for delivery of an injectible fluid with an internally mounted hub and cannula capable of being detached from the syringe cylindrical body withdrawn thereinto, and securely locked in place for disposal.

The syringe has a coupling for detaching the hub and cannula from the cylindrical body and a withdrawal tool attached to the piston face adjacent the cannula and engageable with said coupling during the withdrawal of the hub and cannula into said cylindrical body. At the rear of the cylinder, there is a withdrawn cannula lock for positive securement of the cannula in the withdrawn position. Thereby, after the injectible fluid has been expelled from the fluid chamber, the widhdrawal tool is connected to the hub means and cannula which, in turn, are withdraw into the cylindrical body, and locked securely therewithin.

Further objects and features of the invention will become apparent after reviewing the description of the embodiments together with the drawings which follow.

BRIEF DESCRIPTION OF THE DRAWINGS

FIG. 1 is a sectional view of the syringe of this invention shown with the plunger withdrawn from the barrel in position for injection;

FIG. 2 is a sectional view of the syringe of FIG. 1, but shown with the plunger inserted into the barrel after the injectible fluid has been driven from the syringe;

FIG. 3 is a detailed sectional view of the end of the plunger of FIG. 1 locked into the retractable hub of the cannula assembly, shown partially cutaway to shown the hub in process of being retracted into the barrel;

FIG. 4 is a sectional view of the syringe of FIG. 1, but shown with the cannula assembly fully retracted into the barrwl eith the plunger threadedly connected to the grip end of the barrel;

FIG. 5 is a sectional view of the second embodiment of this invention similar to FIG. 1, but shown with threaded mating portions;

FIG. 6 is a detailed sectional view of the syringe of FIG. 5, similar to FIG. 3, but shown with threaded mating portions;

FIG. 7 is a sectional view of the third embodiment of this invention similar to FIG. 5, but shown with snap-type mating portions; and FIG. 8 is a detailed sectional view of the syringe of FIG. 7, similar to FIG. 6, but shown with snap-type mating portions.

DESCRIPTION OF THE PREFERRED EMBODIMENTS

Referring now to FIG. 1, there is shown generally at 10 an improved disposable syringe of the present invention which comprises a cylindrical body or barrel 12. In syringes of this type, it is common for the barrel to be manufactured from a transparent or substantially transparent material so that injectible fluids therein can be visually monitored. At one end of the cylindrical body 12 a hub 14 is detachably, yet securely, mounted. A cannula or hollow needle 16 is attached to the hub 14 and in the operative position extends away from the cylindrical body 12. When the cannula is mounted to the hub and the hub, in turn, is mounted to the cylindrical body, the assemblage substantially closes one end of the syringe which for descriptive purposes in hereinafter termed the forward end of the syringe. This closure is complete, but for a passageway 18 permitting injectible fluids to flow between the interior of the cylindrical body and the interior of the cannula. In the other end of the cylindrical body 12, a piston 20 is fitted which provides a fluid seal at the juncture thereof and the interior wall 22 of the cylindrical body. Now further describing the piston 20 when positioned within the cylindrical body 12, the piston has two faces, one adjacent the forward end or fluid-chamber face 24 to which a withdrawal tool is mounted, and the rearward face or plunger-mounting face 28 to which a plunger 30 is mounted. When the piston is fitted to the interior wall of the cylindrical body and the plunger is mounted to the rearward face of the piston, a fluid or injectible chamber 32 is defined bounded by the interior wall of the barrel, the forward face of the piston and the rearward face of the hub. The plunger 30 is constructed to extend beyond the mouth of the cylindrical body 12 and to include at the rearward end thereof a thumb rest 34 to facilitate operation of the syringe. In cooperative functional relationship therewith, body or barrel 12 is constructed to include at the rearward lip thereof a grip or finger hold 36.

Referring now to FIGS. 2, 3 and 4, the structure of the disposable syringe is now described which permits further processing of the syringe after the injectible has been expelled from the fluid chamber. The structure includes the detachment mechanism of the hub and cannula portions, the tool for withdrawing of these used portions into the empty fluid chamber, and the lock arrangement of the syringe readied for disposal. The hub of the present invention is constructed with external threads 40 and correspondingly the forward end of cylindrical body 12 is constructed with mating internal threads 42. The hug is further constructed to include a tool-engaging receptacle or coupling 44 for accommodating the withdrawal tool. To facilitate the disconnection of the hub and cannula portions, the fluid-chamber face 24 of piston 20 is equipped with a withdrawal tool 46 for mating with the coupling 44 whereby, in preparation for disposal, the hub and cannula is detached from the cylindrical body and drawn completely into the chamber.

For the first embodiment shown, the withdrawal tool 46 and the hub coupling 44 are now described. A tool head portion 48 is mounted or formed into fluid-chamber face 24. With this added structure, the piston, plunger and thumb rest now take on a dual function and operate as a withdrawl tool. The tool head portion 48 is constructed with one or more leaflike portions 50 with each portion attached along one side 52 thereof. Analogously, but opposed to the tool head portion 48, a hub coupling 44 is mounted onto or formed into the rearward hub face 54. The hub coupling is constructed, in turn of one or more leaflike portions 56 with each portion attached along one side 58 thereof thereby presenting an array opposite to that of tool head portion 48. The hub coupling 44 and the tool head portion 48 are constructed so as to interleave or interlock upon rotary forces applied to the plunger. Further upon continuing such motion, the forces are translated onto the external threads 40 of the hub and cause the hub 14 and cannula 16 to be carried inwardly and reawardly along threads 42 of the cylindrical body. When the rotary motion is continued, the hub 14 and cannula 16 are unscrewed or detached from the cylinder, yet the tool is structured so that the detached portions are still retained or gripped by the interlocking action. Then, once the hub 14 clears the most rearward portion of threads 42, the structure permits withdrawing movement until the disposal lock 60 is encountered. Although several locking arrangements are contemplated at the time of this writing, any of these described herein under various embodiments may be used interchangeably with any of the coupling and detaching arrangements described. In the present instance, a threaded rear portion 62 of the piston 20 is constructed to engage a threaded interior portion 64 of the cylindrical body 12. For simplicity of operation, the threads 62 and 64 are formed so that the same direction of rotation if the plunger is employed for disengaging to hub and for locking the syringe ready for disposal.

Referring now to FIGS. 5 and 6, a second embodiment of the improved disposable syringe is shown. In this embodiment, similar parts are illustrated and, to facilitate understanding thereof, are given reference designators 100 units higher than the first embodiment. Thus, the "cannula 16" of the first embodiment becomes "cannula 116" of the second embodiment.

There is shown generally at 110 an improved disposable syringe of the second embodiment of the present invention which comprises a cylindrical body or barrel 112. At one end of the cylindrical body 112 a hub 114 is detachable, yet securely, mounted. A cannula or hollow needle 116 is attached to the hub 114 and in the operative position extends away from the cylindrical body 112. When the cannula is mounted to the hub and the hub, in turn, is mounted to the cylindrical body, the assemblage substantially closes one end of the syringe. This closure is complete, but for a passageawy 118 permitting injectible fluids to flow between the interior of the cylindrical body and the interior of the cannula. In the other end of the cylindrical body 112, a piston 120 is fitted which provides a fluid seal between the interior wall 122 of the cylindrical body. The piston 120 has two faces—one adjacent the forward end or fluid-chamber face 124 to which a withdrawal tool is mounted, and the rearward face or plunger-mounting face 128 to which a plunger 130 is mounted. When the piston is fitted to the interior wall of the cylindrical body and the plunger is mounted to the rearward face of the piston, a fluid or injectible chamber 132 is defined bounded by the interior wall of the barrel, the forward face of the piston and the rearward face of the hub. the plunger 130 is constructed to extend beyond the mouth of the cylindrical body 112 and to include at the rearward end thereof a thumb rest 134 to facilitate operation of the syringe. In cooperative functional relationship therewith, body or barrel 112 is constructed to include at the rearward lip thereof a grip or finger hold 136.

As with the first embodiment, the structure of the second embodiment includes a detachment mechanism for the hub and cannula portions; a tool for the withdrawal of these used portions; and a lock arrangement for use in disposal of the syringe. The hub of the second embodiment is constructed with a threaded fitting 140 and correspondingly the forward end of cylindrical body 112 is constructed with a mating fitting 142. The hub is further constructed to include a threaded receptacle or coupling 144 for accommodating the withdrawl tool 146. To facilitate the disconnection of the hub and cannula portions, the fluid-chamber face 124 of piston 120 is equipped with a threaded connector 146 for mating with the coupling 144 whereby, in preparation for disposal, the hub and cannula is detached from the cylindrical body and drawn completely into the chamber.

For the second emobdiment shown, the withdrawal tool 146 and the hub coupling 144 are now described. A tool head portion 148 is constructed with a threaded outer portion 150 for mating with a hub coupling 144. In the present invention, the hub coupling threads 152 are constructed so that, upon the tool head portion "bottoming out" the tool rotation can be continued in the same direction and cause the hub 114 and cannula 116 assembly to be unthreded from the cylindrical body 112 and to be withdrawn into the cylindrical body 112. Thereafter the withdrawal tool is constructed to permit the hub and cannula to be pulled rearwardly until it is wholly within the cylindrical body. At such point, the interior of the cylindrical body proximate thumb rest 134 is structured to include locking threads 160 for mating with plunger locking threads 162. The lock is engaged by rotating the plunger in the same direction as for withdrawal. While the above embodiment is described with threaded portions all requiring the same direction of rotation for simplicity of operation, it is understand that various configurations may obtain without departing from the spirit of the invention.

Referring now to FIGS. 7 and 8, there is shown generally at 210 an improved disposable syringe of the third embodiment of the present invention. In describing the third embodiment similar parts are given similar reference designators 200 units higher than the first embodiment. The syringe is constructed to include a cylindrical body or barrel 212. At one end of the cylindrical body 212 a hub 214 is detachable, yet securely, mounted. A cannula or hollow needle 216 is atached to the hub 214 and in the operative position extends away from the cylindrical body 212. When the cannula is mounted to the hub and the hub, in turn, is mounted to the cylindrical body, the assemblage substantially closes one end of the syringe This closure is complete, but for a passageway 218 permitting injectible fluids to flow between the interior of the cylindrical body and the interior of the cannula. In the other end of the cylindrical body 212, a piston 220 is fitted which provides a fluid seal between the interior wall 222 of the cylindrical body. The piston 220 has two faces—one adjacent the forward end or fluid-chamber face 224 to which a withdrawal tool is mounted, and the rearward face or plunger-mounting face 228 to which a plunger 230 is mounted. When the piston is fitted to the interior wall of the cylindrical body and the plunger is mounted to the rearward face of the piston, a fluid or injectible chamber 232 is defined bounded by the interior wall of the barrek, the forward face of the piston and the rearward face of the hub. The plunger 230 is constructed to extend beyond the mouth of the cylindrical body 212 and to include at the rearward end thereof a thumb rest 234 to facilitate operation of the syringe. In cooperative functional relationship therewith, body or barrel 212 is constructed to include at the rearward lip thereof a grip or finger hold 236.

The hub 214 of the third embodiment is attached to the forward end of the cylindrical body 212 by press-fitting therewithin and, upon assembling to the interior of the cylindrical body, the hub rim 238 is fitted to an annular, hub-retaining groove 240. The hub rim 238 is constructed from a resilient material which conforms to the groove 240. At the central portion of the hub 234, a receptacle or coupling 244 is constructed to accommodate the withdrawal tool. To facilitate the disconnection of the hub and cannula portions, the fluid-chamber face 224 of piston 220 is equipped with a withdrawal tool 246 for mating with the coupling 244.

For the third embodiment shown, the withdrawal tool 246 and the hub coupling 244 are now described. A tool head portion 248 is mounted or formed into fluid-chamber face 224. The tool head portion 248 is constructed to snap-fit onto coupling 244 and thereafter to act cooperatively with piston and plunger as a pulling tool. When the plunger is pulled rearwardly, the coupling is of sufficient strength to overcome the press fit of the hub-rim. Then, once the hub 214 clears the most rearward portion of groove 240, the structure permits withdrawing movement until the resilient locking member 260 is encountered. In the third embodiment, a grooved rear portion 262 of the piston 220 is constructed to engage a stpped rim 264 on the wall 222 of the cylindrical body 212.

What is claimed is:

1. A disposable syringe for delivery of an injectible fluid comprising, in combination:
    a cylindrical body;
    hub means for mounting a cannula attached to one end thereof;
    a cannula attached to said hub means extending outwardly from said cylindrical body, said cannula and hub means substantially closing said one end of the cylindrical body and having a passageway for said injectible fluid between the interiors of the cannula and the cylindrical body;
    a piston sealingly engaging the interior wall of said cylindrical body defining a fluid chamber between the piston face adjacent the cannula and the hub face adjacent the piston;
    plunger means for reciprocating said piston toward and away from said cannula, with one end attached to said piston and the other end thereof extending beyond the open end of said cylindrical body;
    coupling means for detaching said hub means and cannula from said cylindrical body;
    withdrawal tool means attached to the piston face adjacent the cannula and engageable with said coupling means during the withdrawal of the hub means and cannula into said cylindrical body; and,
    withdrawn cannula lock means for positive securement of the cannula in the withdrawn position, said withdrawn cannula lock means having a male locking threaded portion attached to the rear of the piston and a female locking threaded portion attached adjacent the open end of said cylindrical body;
    whereby, after the injectible fluid has been expelled from the fluid chamber, the withdrawal tool is connected to the hub means and cannula which, in turn, are withdrawn into the cylindrical body, and locked securely therewithin.

2. A disposable syringe as described in claim 1 wherein said coupling means further comprises:
    at least one coupling leaf portion attached at one edge thereof to the interior face of said hub means, the line of attachment being substantially radial therealong;
    and wherein said withdrawal tool further comprises:
    at least one withdrawal leaf portion attached at one edge thereof to the interior face of the withdrawal tool, the line of attachment being substantially radial therealong;
    whereby, after the plunger means is fully inserted into the fluid chamber and rotated in a predetermined direction the leaf portions are engageable the one interlockingly with the other.

3. A disposable syringe as described in claim 2 wherein the hub means has a threaded portion threadedly engaged to the interior of the cylindrical body.

4. A disposable syringe as described in claim 3 wherein the threaded portion is disengageable from the cylindrical body by further rotation in said predetermined direction.

5. A disposable syringe as described in claim 4 wherein the threaded portion transports the hub means and cannula attached thereto into the cylindrical body by said rotational motion and thereafter by translational motion of the withdrawl tool.

6. A disposable syringe as described in claim 1 wherein, upon completion of said translational motion of the withdrawal tool, the hub means and cannula are locked in the cylindrical body by threadedly engaging said male locking threaded portion and said female locking thread.

7. A disposable syringe for delivery of an injectible fluid comprising, in combination:
   a cylindrical body having at one end thereof an internally disposed female threaded portion,
   hub means for mounting a cannula having an externally disposed male threaded portion and sealingly engageable with said female threaded portion;
   a cannula attached to said hub means extending outwardly from said cylindrical body, said cannula and hub means substantially closing said one end of the cylindrical body and having a passageway for said injectible fluid between the interiors of the cannula and the cylindrical body; cylindrical body defining a fluid chamber between the piston face adjacent the cannula and the hub face adjacent the piston;
   plunger means for reciprocating said piston toward and away from said cannula, with one end attached to said piston and the other end thereof extending beyond the open end of said cylindrical body;
   coupling means for detaching said hub means and cannula from said cylindrical body;
   withdrawal tool means attached to the piston face adjacent the cannula and engageable with said coupling means during the withdrawl of the hub means and cannula into said cylindrical body; and,
   withdrawn cannula lock means for positive securement of the cannula in the withdrawn position, said withdrawn cannula lock means having a male locking threaded portion attached to the rear of the piston and a female locking threaded portion attached adjacent the open end of said cylindrical body;
   whereby, after the injectible fluid has been expelled from the fluid chamber, the withdrawal tool is connected to the hub means and cannula which, in turn, are withdrawn into the cylindrical body, and locked securely therewithin.

8. A disposable syringe as described in claim 7 wherein said coupling means further comprises:
   at least one coupling leaf portion attached at one edge thereof to the interior face of said hub means, the line of attachment being substantially radial therealong;
   and wherein said withdrawal tool further comprises:
   at least one withdrawal leaf portion attached at one edge thereof to the interior face of the withdrawal tool, the line of attachment being substantially radial therealong;
   whereby, after the plunger means is fully inserted into the fluid chamber and rotated in a predetermined direction the leaf portions are engageable the one interlockingly with the other.

9. A disposable syringe as described in claim 8 wherein the threaded portion of the hub means is disengageable from the cylindrical body by further rotation in said predetermined direction.

10. A disposable syringe as described in claim 9 wherein the threaded portion transports the hub means and cannula attached thereto into the cylindrical body by said rotational motion and thereafter by translational motion of the withdrawal tool.

11. A disposable syringe as described in claim 7 wherein, upon completion of said translational motion of the withdrawal tool, the hub means and cannula are locked in the cylindrical body by threadedly engaging said male locking threaded portion and said female locking thread.

12. A disponsable syringe as described in claim 7 wherein said coupling means further comprises:
   a cuplike coupling attached to the interior face of said hub means having a female internally threaded portion engageable with the opposite hand as the female threaded portion of the cylindrical body;
   and wherein said withdrawal tool further comprises:
   a withdrawal tool head attached to the interior face of the withdrawal tool having a male threaded portion for mating with said cuplike coupling;
   whereby after the plunger means is fully inserted in the fluid chamber and rotated in a predetermined direction, the cuplike coupling and tool head are engageable the one threading into the other.

13. A disposable syringe as described in claim 12 wherein the threaded portion of the hub means is disengageable from the cylindrical body by further rotation in said predetermined direction.

14. A disposable syringe as described in claim 13 wherein the threaded portion transports the hub means and cannula attached thereto into the cylindrical body by said rotational motion and thereafter by translational motion of the withdrawal tool.

15. A disposable syringe as described in claim 14 wherein, upon completion of said translational motion of the withdrawal tool, the hub means and cannula are locked in the cylindrical body by threadedly engaging said male locking threaded portion and said female locking thread.

16. A disposable syringe for delivery of an injectible fluid comprising, in combination:
   a cylindrical body;
   hub means for mounting a cannula attached to one end thereof having a threaded portion threadedly engagable to the interior of the cylindrical body and disengageable from the cylindrical body by further rotation in a predetermined direction;
   a cannula attached to said hub means extending outwardly from said cylindrical body, said cannula and hub means substantially closing said one end of the cylindrical body and having a passageway for said injectible fluid between the interiors of the cannula and the cylindrical body;
   a piston sealingly engaging the interior wall of said cylindrical body defining a fluid chamber between the piston face adjacent the cannula and the hub face adjacent the piston;
   plunger means for reciprocating said piston toward and away from said cannula, with one end attached to said piston and the other end thereof extending beyond the open end of said cylindrical body;
   coupling means for detaching said hub means and cannula from said cylindrical body, said coupling means having at least one coupling leaf portion attached at one edge thereof to the interior face of said hub means, the line of attachment being substantially radial therealong;
   withdrawal tool means for transporting the hub means and cannula attached thereto into the cylindrical body, attached to the piston face adjacent the cannula and engageable with said coupling means during the withdrawal of the hub means and cannula into said cylindrical body, said withdrawal tool means having at least one withdrawal leaf portion attached at one edge thereof to the interior face of the withdrawal tool means, the line of attachment being substantially radial therealong; and, withdrawn cannula lock means for positive securement of the cannula in the withdrawn position, said withdrawn cannula lock means having a male locking threaded portion attached to the rear of the piston and a female locking threaded portion attached adjacent the open end of said cylindrical body;

whereby, after the injectible fluid has been expelled from the fluid chamber, the withdrawal tool means is connected to the hub means and cannula by full insertion of the plunger means into the fluid chamber and rotation thereof in a predetermined direction with the leaf portions engaging interlockingly the one with the other and said hub means and cannula are in turn, withdrawn into the cylindrical body, and locked securely therewithin.

17. A disposable syringe as described in claim 16 wherein, upon completion of said translational motion of the withdrawal tool, the hub means and cannula are locked in the cylindrical body by threadedly engaging said male locking threaded portion and said female locking thread.

18. A disposable syringe for delivery of an injectible fluid comprising, in combination:

a cylindrical body;

hub means for mounting a cannula attached to one end thereof;

a cannula attached to said hub means extending outwardly from said cylindrical body, said cannula and hub means substantially closing said one end of the cylindrical body and having a passageway for said injectible fluid between the interiors of the cannula and the cylindrical body;

a piston sealingly engaging the interior wall of said cylindrical body defining a fluid chamber between the piston face adjacent the cannula and the hub face adjacent the piston;

plunger means for reciprocating said piston toward and away from said cannula, with one end attached to said piston and the other end thereof extending beyond the open end of said cylindrical body;

coupling means for detaching said hub means and cannula from said cylindrical body; said coupling means having a threaded portion at the interior face of said hub means.

withdrawal tool means for transporting the hub means and cannula attached thereto into the cylindrical body, attached to the piston face adjacent the cannula and engageable with said coupling means during the withdrawal of the hub means and cannula into said cylindrical body, said withdrawal tool means having a threaded portion at the interior face of the withdrawal tool means for cooperative functional relationship with the threaded portion of said coupling means; and, withdrawn cannula lock mean for positive securement of the cannula in the withdrawn position, said withdrawn cannula lock means having a male locking threaded portion attached to the rear of the piston and a female locking threaded portion attached adjacent the open end of said cylindrical body;

whereby, after the injectible fluid has been expelled from the fluid chamber, the withdrawal tool means is connected to the hub means and cannula by full insertion of the plunger means into the fluid chamber and rotation thereof in a predetemrined direction with the leaf portions engaging interlockingly the one with the other and said hub means and cannula are, in turn, withdrawn into the cylindrical body, and locked securely therewithin.

19. A disposable syringe is described in claim 18 wherein, upon completion of said translational motion of the withdrawal tool, the hub means and cannula are locked in the cylindrical body by threadedly engaging said male locking threaded portion and said female locking thread.

20. A disposable syringe for delivery of an injectible fluid comprising, in combination:

a cylindrical body;

hub means for mounting a cannula attached to one end thereof;

a cannula attached to said hub means extending outwardly from said cylindrical body, said cannula and hub means substantially closing said one end of the cylindrical body and having a passageway for said injectible fluid between the interiors of the cannula and the cylindrical body;

a piston sealingly engaging the interior wall of said cylindrical body defining a fluid chamber between the piston face adjacent the cannula and the hub face adjacent the piston;

plunger means for reciprocating said piston toward and away from said cannula, with one end attached to said piston and the other end thereof extending beyond the open end of said cylindrical body;

coupling means for detaching said hub means and cannula from said cylindrical body, said coupling means having a cuplike portion attached to the interior face of said hub means having a female internally threaded portion engageable with the opposite hands as the female threaded portion of the cylindrical body;

withdrawal tool means for transporting the hub means and cannula attached thereto into the cylindrical body, attached to the piston face adjacent the cannula and engageable with said coupling means during the withdrawal of the hub means and cannula into said cylindrical body, said withdrawal tool means having a threaded portion at the interior face of the withdrawl tool means for cooperative functional relationship with the cuplike portion of said coupling means; and, withdrawn cannula lock means for positive securement of the cannula in the withdrawn position, said withdrawn cannula lock means having a male locking threaded portion attached to the rear of the piston and a female locking threaded portion attached adjacent the open end of said cylindrical body;

whereby, after the injectible fluid has been expelled from the fluid chamber, the withdrawal tool is connected to the hub means and cannula which, in turn, are withdrawn into the cylindrical body, and locked securely therewithin.

21. A disposable syringe as described in claim 20 wherein, upon completion of said translational motion of the withdrawal tool, the hub means and cannula are locked in the cylindrical body by threadedly engaging said male locking threaded portion and said female locking thread.

22. A disposable syringe for delivery of an injectible fluid comprising, in combination:
   a cylindrial body;
   hub means for mounting a cannula attached to one end thereof;
   a cannula attached to said hub means extending outwardly from said cylindrical body, said cannula and hub means substantially closing said one end of the cylindrical body and having a passageway for said injectible fluid between the interiors of the cannula and the cylindrical body;
   a piston sealingly engaging the interior wall of said cylindrical body defining a fluid chamber between the piston face adjacent the cannula and the hub face adjacent the piston;
   plunger means for reciprocating said piston toward and away from said cannula, with one end attached to said piston and the other end thereof extending beyond the open end of said cylindrical body;
   coupling means for detaching said hub means and cannula from said cylindrical body;
   withdrawal tool means attached to the piston face adjacent the cannula and engageable with said coupling means during the withdrawal of the hub means and cannula into said cylindrical body; and,
   withdrawn cannula lock means for positive securement of the cannula in the withdrawn position, said withdrawn cannula lock means including a resilient male locking member with an annular grooved portion thereon attached to the rear of the piston and a female locking aperture means including a rim with diameter corresponding to said annular grooved portion in the open end of said cylindrical body;
   whereby, after the injectible fluid has been expelled from the fluid chamber, the withdrawal tool is connected to the hub means and cannula which, in turn, are withdrawn into the cylindrical body, until the resilient male locking member is drawn through the female locking aperture and the annular grooved portion snaps onto the rim of the aperture means, securely locking the hub means and cannula within the cylindrial body.

* * * * *